United States Patent
Wetzig

(10) Patent No.: US 8,616,046 B2
(45) Date of Patent: Dec. 31, 2013

(54) HYDROGEN SENSOR

(75) Inventor: Daniel Wetzig, Köln (DE)

(73) Assignee: Inficon GmbH (DE)

( * ) Notice: Subject to any disclaimer, the term of this patent is extended or adjusted under 35 U.S.C. 154(b) by 207 days.

(21) Appl. No.: 13/380,471

(22) PCT Filed: Jun. 14, 2010

(86) PCT No.: PCT/EP2010/058308
§ 371 (c)(1),
(2), (4) Date: Dec. 22, 2011

(87) PCT Pub. No.: WO2010/149519
PCT Pub. Date: Dec. 29, 2010

(65) Prior Publication Data
US 2012/0090380 A1    Apr. 19, 2012

(30) Foreign Application Priority Data
Jun. 24, 2009 (DE) .......................... 10 2009 030 180

(51) Int. Cl.
*G01N 7/10* (2006.01)
*G01M 3/00* (2006.01)
*G01M 3/04* (2006.01)

(52) U.S. Cl.
USPC ........................................ 73/31.04; 73/40.7

(58) Field of Classification Search
USPC ............................... 73/31.04, 40.7
See application file for complete search history.

(56) References Cited

U.S. PATENT DOCUMENTS

| 2,811,037 | A  | * | 10/1957 | Beard ........................ 73/31.04 |
| 3,731,523 | A  |   | 5/1973  | Vissers et al. |
| 3,866,460 | A  | * | 2/1975  | Pearce, Jr. ................... 73/19.05 |
| 4,112,736 | A  | * | 9/1978  | Wheldon et al. ............ 73/31.04 |
| 7,266,991 | B2 |   | 9/2007  | Bley |
| 2005/0188845 | A1 | * | 9/2005 | Yamaguchi et al. ............. 96/11 |
| 2008/0202211 | A1 | * | 8/2008 | Wetzig ........................... 73/40.7 |
| 2009/0173141 | A1 | * | 7/2009 | Grosse Bley et al. ........ 73/25.05 |

FOREIGN PATENT DOCUMENTS

DE    198 33 601 C1    12/1999
DE    100 31 882 A1     1/2002

OTHER PUBLICATIONS

On the gas species dependence of Pirani vacuum gauges; Karl Jousten; J. Vac. Sci. Technol. A 26(3), May/Jun. 2008 of the American Vacuum Society, pp. 352-359 (8 pages).
International Search Report/Written Opinion for PCT Application No. PCT/EP2010/058308; mailed Sep. 13, 2011; 7 pages.

* cited by examiner

*Primary Examiner* — Lisa Caputo
*Assistant Examiner* — Punam Roy
(74) *Attorney, Agent, or Firm* — Hiscock & Barclay, LLP

(57) ABSTRACT

A hydrogen sensor includes a housing, which is closed off by a membrane that is made of palladium and selectively only pervious to hydrogen. The housing is evacuated and contains a Pirani pressure sensor. The membrane and the Pirani pressure sensor are each attached to a carrier. Both carriers are joined directly next to one another or kept at a distance by a connection piece. The hydrogen sensor has a high sensitivity and a low response time due to the relatively large membrane surface and the low housing volume. It can be produced in a small size and integrated in the handle of a sniffer-type leak indicator.

8 Claims, 1 Drawing Sheet

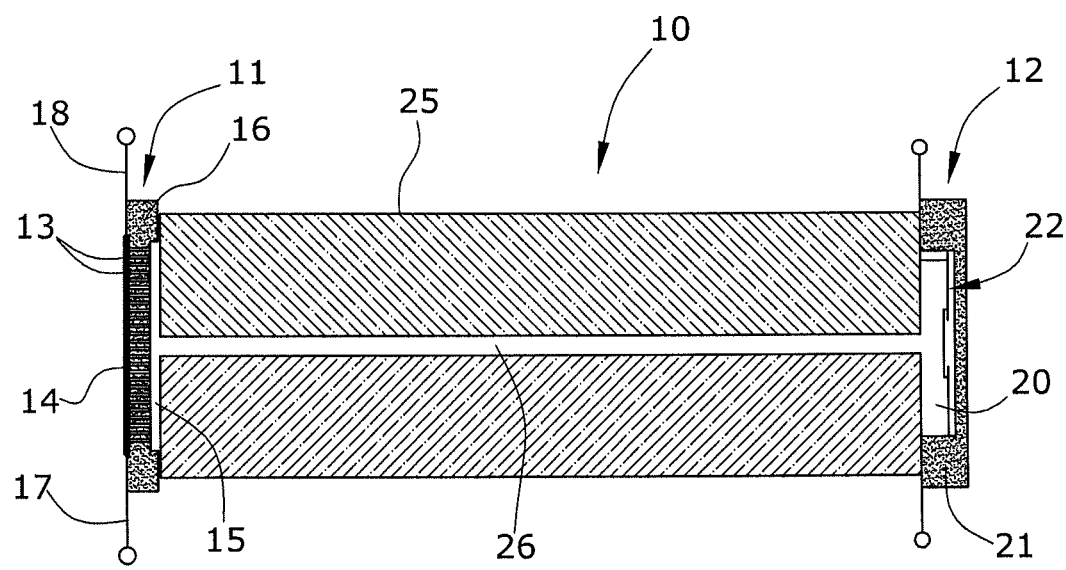

HYDROGEN SENSOR

CROSS REFERENCE TO RELATED APPLICATIONS

Pursuant to 35 USC §371, this application is a National Stage of International Application No. PCT/EP2010/058308, filed Jun. 14, 2010, which claims priority to German Patent Application No. 102009030180.1, filed Jun. 24, 2009 under applicable paragraphs of 35 USC §119, wherein the entire contents of each above-noted document is herein incorporated by reference.

TECHNICAL FIELD

The invention refers to a hydrogen sensor with a pressure-tight housing closed off by a membrane of palladium and includes a pressure sensor.

BACKGROUND AND RELATED ART

A known hydrogen sensor is described in WO 2006/008253 A1 (Inficon). This hydrogen sensor has a membrane that is selectively permeable to hydrogen and closes off a pressure-tight housing. The housing contains a Penning pressure sensor with two parallel cathode plates between which an anode ring is arranged. A voltage source supplies a direct voltage that is applied between the cathode plates and the anode ring. The magnetic field required for a Penning-type discharge is generated by a permanent magnet provided outside the closed housing. A getter pump is connected to the housing, which draws hydrogen and reduces the hydrogen partial pressure. The detection chamber of the housing is connected to the getter pump through a throttling channel. If hydrogen from the atmosphere enters the detection chamber through the membrane, which is selectively permeable to hydrogen, the pressure in the detection chamber rises. Since the hydrogen reaches the getter pump only with a delay due to the throttling channel, the pressure in the detection chamber rises. This pressure increase is detected by the pressure sensor and is evaluated as an intrusion of hydrogen. Even under steady-state conditions, the partial pressure in the detection chamber is lower than the partial pressure of the surroundings.

In DE 100 31 882 A1 (Leybold) a sensor for helium or hydrogen is described which comprises a vacuum-tight housing with a selectively acting passage for the gas to be detected. The housing is made of glass and the selectively acting passage is a membrane of a silicon material on which a silicon disc with openings and a heating are arranged. The housing holds a Penning sensor. The housing is not connected to a vacuum pump. The Penning-type discharge of the Penning sensor additionally acts as a getter pump.

In J. Vac. Sci. Technol. A 26(3), May/June 2008 of the American Vacuum Society, pages 352-359, an article titled "On the gas species dependence of Pirani vacuum gauges" by Karl Jousten was published which describes the principle of the Pirani pressure sensor. This is an apparatus that measures the thermal conductivity of gases and thereby determines pressure. This benefits from the fact that thermal conductivity is proportional to pressure. The heat transmission from a heating element through surrounding gas to an enclosure of a more or less constant temperature is measured. The heating element is a part of a Wheatstone bridge operated such that the heating power required to maintain the temperature is measured. With other Pirani sensors, the heating power is maintained constant and the resistance or the temperature of the heating element is measured as the pressure indicator. Pirani pressure sensors have to be calibrated appropriately for the respective gas, since gas-dependent correction factors must be taken into account when evaluating the signals.

SUMMARY

It is an object of the present invention to provide a hydrogen sensor with a high sensitivity to hydrogen and a short reaction time which can be produced with small dimensions.

The hydrogen sensor according to one aspect comprises an evacuated, pressure-tight, pump-less housing. This means that the housing is not connected to a pump, e.g. a getter pump. The housing is closed with a palladium membrane that is selectively permeable only to hydrogen. As a consequence, an overall pressure prevails in the housing that is equal to the partial pressure of the hydrogen in the ambient atmosphere.

According to an aspect, the palladium membrane is arranged on a first carrier and a non-gas-consuming pressure sensor is arranged on a second carrier. Both carriers are either connected directly or are kept at a distance by means of a glass tube. Both the palladium membrane and the Pirani pressure sensor comprise a heating, but they are thermally decoupled from each other so that the heat transport from the heating element of the pressure sensor is not disturbed by the heating of the palladium membrane. It should be taken into account that the palladium membrane is heated to a constant temperature so that the thermal effects caused thereby in the housing are constant.

According to the invention, a pressure sensor is used that consumes no gas. These sensors can include thermal conduction gauges and capacitance gauges. A Pirani pressure gauge is a thermal conduction gauge. These further include gauges which measure the thermal conduction from one conductor through another conductor through the surrounding gas. Thermal conduction depends on gas pressure. Capacitance gauges comprise a membrane onto which gas pressure acts from one side. The membrane is part of a capacitor whose capacitance varies as a function of pressure. The variation in capacity is measured electrically. In contrast thereto, a Penning pressure sensor is gas consuming. All ionizing sensors belong to the gas-consuming sensors.

A thermal conduction gauge, such as the Pirani gauge, has the advantages of high sensitivity and small structural size. No pump or suction capability acts in the housing. The same $H_2$ partial pressure prevails inside the housing as in the sensor surroundings. The time constant τ of the sensor, i.e., the time to a pressure equalization of 63%, is primarily determined by the ratio of volume and conductance value of the membrane:

$$\tau = \text{volume/conductance value}.$$

For a hydrogen concentration of c=1 ppm at atmospheric pressure, the hydrogen partial pressure is $p_{H2}=1\times10^{-3}$ mbar. This pressure can be detected reliably by commercial Pirani sensors. With the MikroPirani of the company MKS, total pressures to below $10^{-4}$ mbar can be detected. Higher Pirani filament temperatures allow for a further increase in sensitivity.

The advantages of the invention consist in high sensitivity, a short time constant, the avoidance of cross-sensitivity to other gases than hydrogen, and longevity. A further essential advantage is the small size that allows an integration of the hydrogen sensor into the handle of a sniffer leak detector. Such a sniffer leak detector only requires a gas conveying device to draw atmosphere and requires no vacuum pump for test gas analysis. The hydrogen sensor operates under atmospheric pressure.

In the hydrogen sensor of the present invention, without suction capability, the $H_2$ partial pressure in the housing is equal to the ambient partial pressure. The time constant of the sensor is given by the ratio of the interior volume of the sensor cells V and the hydrogen conductance value $L_{membrane}$ of the palladium membrane:

$$\tau_{63} = \frac{V}{L_{membrane}} \quad (1)$$

If a suction capability S existed in the interior of the sensor, the ratio of the partial pressure in the surroundings $p_1$ to the partial pressure inside the sensor $p_0$ would be as follows:

$$\frac{p_1}{p_0} = \frac{S}{L} + 1, \quad (2)$$

where L is the conductance value of the membrane.

In this case, the sensor time constant would be given by the ratio of the sensor cell volume V and the suction capability S:

$$\tau_{63} = \frac{V}{S} \quad (3)$$

A suction capability inside the sensor would allow for a rather large sensor volume without the sensor time constant exceeding the limit of 1 s, however, in this case, the hydrogen partial pressure inside the sensor is reduced (see eq. 2) so that a Pirani system could not detect the pressure with sufficient accuracy.

According to the invention, a sensor time constant less than 1 s is achieved for a sensor volume of about 1 $cm^3$ without suction capability inside the sensor. In such a system, the total pressure can be measured with a micromechanical Pirani system. The sensitivity of a Pirani system in the sensor for the detection of 1 ppm of hydrogen at an ambient pressure of 1000 mbar is sufficient. The dependence of the Pirani detection on the gas species has positive effects on the detection sensitivity in the case of hydrogen.

With a thermal conduction gauge, hydrogen can be detected in a more sensitive manner than nitrogen. The thermal conduction coefficient of hydrogen is higher by the factor 7.2 than that of $N_2$. Moreover, a heating filament can be operated at a higher temperature in a pure hydrogen atmosphere, whereby the detection limit is also favorably influenced.

The palladium (Pd) material of which the selectively hydrogen-permeable wall of the housing is made has the effect that it is permeable only to hydrogen and its isotopes ($H_2$, $D_2$, $T_2$, HD, HT and DT). For all other elements, the permeability is negligibly low. Thus, hydrogen can be separated from other gases. The palladium membrane is present on a silicon carrier and forms a palladium membrane chip with the same. In a practical embodiment of the chip, the palladium membrane has a high hydrogen conductance value in the range between 9.6 and 1.7 $cm^3$/s at 300° C. The silicon carrier serves to support the thin palladium membrane so that the same can resist atmospheric pressure. The palladium membrane preferably has a thickness of less than 5 μm, in particular less than 2 μm. The first carrier bearing the membrane has openings or windows of 200 μm in width and can resist a total differential pressure of P>1000 mbar.

If a porous silicon is used as the carrier material, a considerably thinner membrane thickness is possible. The conductance value of the membrane is inversely proportional to its thickness. However, other carrier materials are possible, such as steel or palladium.

In an encapsulated volume of 1 $cm^3$ closed off by a Pd membrane with an area of 1.5 $cm^2$ and a thickness of 1 μm, the hydrogen partial pressure of the surroundings occurs with a time constant of $\tau=1$ s. With a smaller sensor volume and/or a thinner Pd membrane surface even shorter time constants can be achieved. This also offers the possibility to use gas modulation techniques in a leak detector.

BRIEF DESCRIPTION OF THE DRAWINGS

The following is a detailed description of an embodiment of the invention with reference to the sole FIGURE of the drawings, in which FIG. 1 illustrates an embodiment of a hydrogen sensor according to the present invention.

DETAILED DESCRIPTION

Referring to FIG. 1, the hydrogen has a pressure-tight housing 10 that is closed off at one end by a first carrier 11 of silicon and at the opposite end by a second carrier 12 of silicon. The carriers form the end walls of the housing. The housing 10 holds a gas volume that is as small as possible.

The first carrier 11 is a plate made of silicon material whose thickness is large enough for the plate to resist atmospheric pressure. The first carrier 11 is provided with numerous openings 13. These openings are throughholes. The palladium membrane 14 is provided on the outer side of the first carrier 11. The membrane is a thin film with a thickness of about 1 μm.

On the inner side of the housing, the first carrier 11 is provided with a recess 15 surrounded by a projecting rim 16. The membrane 14 an be heated either by a direct current flow or it may be provided with an additional heating layer. According to another possibility, the first carrier 11 is used as an ohmic heater or the membrane is heated using a radiant heater. In the present embodiment, the current connectors 17, 18 for heating current are provided at the membrane 14.

The second carrier 12 is also made of silicon. It has a recess 20 in the side facing the housing interior, which recess is surrounded by a rim 21. A Pirani sensor 22 is fastened in the recess 20 on the inner side of the end wall. The sensor consists of filaments that form a Wheatstone bridge, for instance. A heating element is formed on the Pirani sensor, whose heat is transported by the hydrogen passing the membrane 14. For the structure and the functioning of the Pirani pressure sensor 22 reference is made to J. Vac. Sci. Technol. A 26(3), May/June 2008, pages 352-359.

The carriers 11 and 12 may be joined directly to each other. Thereby, a minimum possible encapsulated volume is achieved. This allows a very fast sensor reaction. For a volume of 50 $nm^3$, a sensor time constant of 50 ms can be achieved. Joining the membrane and the Pirani filament to the respective carrier can be done using bonding methods if silicon is used. However, adhesives may also be used that have a sufficient temperature resistance.

In order that the temperature of the heated membrane 14 has only little effect on the operation of the Pirani pressure sensor 22, the first carrier 11 and the second carrier 12 are spaced apart by means of a connection piece 25 which, in the present case, is a glass tube. The connection piece 25 is elongate and includes a longitudinal channel 26 of small cross section. The cross-sectional area of the channel 26 is at most one fifth of the surface area of the membrane 14. Thereby, the volume of the housing 10 is maintained small so that short reaction times of the sensor are obtained.

The volume of the housing 10 is evacuated during the manufacture of the sensor. When the sensor is in use, hydrogen from the atmosphere can penetrate the membrane 14, whereby a total pressure develops inside the housing 10 that is equal to the hydrogen partial pressure outside the housing. This pressure is measured by the Pirani pressure sensor 22.

The hydrogen sensor is particularly suited for a sniffer leak detector comprising a stationary main device and a handle movable with respect to the main device, the sniffer tip being provided at the handle. The hydrogen sensor is made with dimensions so small that it can be integrated in the handle of the sniffer leak detector. With a gas glow of 30 sccm and the use of forming gas (5%-$H_2$) as the test gas, a leakage rate of $5 \times 10^{-6}$ mbar×l/s can be detected with a partial pressure detection limit of $5 \times 10^{-4}$ mbar.

In the sniffer application, the hydrogen proportion of about 0.5 ppm in the air has positive effects on the signal detection. Due to this, the hydrogen partial pressure offset of $5 \times 10^{-4}$ is always measured. The characteristic of the Pirani pressure sensor allows a higher signal resolution at a constant pressure offset s that pressure changes less than $5 \times 10^{-4}$ mbar can be detected.

The invention claimed is:

1. A hydrogen sensor comprising a pressure-tight pumpless housing closed off by a membrane of palladium, said membrane being arranged on a first carrier having a plurality of openings, and comprising a non gas consuming pressure sensor with a second carrier, wherein the first and the second carrier are one of joined directly to each other and spaced apart by a connection piece.

2. The hydrogen sensor of claim 1, wherein the palladium membrane has a thickness of less than 5 μm.

3. The hydrogen sensor of claim 1, wherein the effective surface area of the membrane is at least 1.5 $cm^2$, and said connection piece includes a channel with a cross section of at most one fifth of the effective membrane surface area.

4. The hydrogen sensor of claim 1, wherein at least one of the first and second carrier is made of porous silicon.

5. The hydrogen sensor of claim 1, wherein said hydrogen sensor is integrated in the handle of a sniffer leak detector.

6. The hydrogen sensor of claim 1, wherein the non gas consuming pressure sensor is a capacitance manometer.

7. The hydrogen sensor of claim 1, wherein the pressure sensor is a heat conduction pressure sensor.

8. The hydrogen sensor of claim 7, wherein the heat conduction pressure sensor is a Pirani pressure sensor.

* * * * *